United States Patent [19]

Walloch

[11] Patent Number: 4,905,704
[45] Date of Patent: Mar. 6, 1990

[54] METHOD AND APPARATUS FOR DETERMINING THE MEAN ARTERIAL PRESSURE IN AUTOMATIC BLOOD PRESSURE MEASUREMENTS

[75] Inventor: Richard A. Walloch, Beaverton, Wash.

[73] Assignee: SpaceLabs, Inc., Redmond, Wash.

[21] Appl. No.: 299,776

[22] Filed: Jan. 23, 1989

[51] Int. Cl.$^4$ .............................................. A61B 5/02
[52] U.S. Cl. ................................... 128/682; 128/681
[58] Field of Search ............... 128/672, 677, 680–683, 128/685–685, 684

[56] References Cited

U.S. PATENT DOCUMENTS

| | | | |
|---|---|---|---|
| 4,543,962 | 10/1985 | Medero et al. | 128/680 X |
| 4,546,775 | 10/1985 | Medero | 128/680 X |
| 4,727,884 | 3/1988 | Link | 128/677 X |
| 4,754,761 | 7/1988 | Ramsey et al. | 128/681 X |
| 4,796,184 | 1/1989 | Bahr et al. | 128/682 X |

*Primary Examiner*—Angela D. Sykes
*Attorney, Agent, or Firm*—Seed and Berry

[57] ABSTRACT

A method and apparatus for determining the mean arterial pressure in an automatic blood pressure measuring system in which a table of data is obtained of cuff pressures and the amplitude of oscillometric pulses produced at each cuff pressure. The oscillometric pulses having the greatest amplitude and a reference cuff pressure at which such oscillometric pulses occurred are first identified from the table. Respective first and second cuff pressures that are above and below the reference cuff pressure and have a amplitude of 90% of the largest oscillometric pulses are then calculated by interpolating between the measured data in the table, and the mean arterial pressure is then calculated as the average of the first and second cuff pressures.

15 Claims, 7 Drawing Sheets

METHOD AND APPARATUS FOR DETERMINING THE MEAN ARTERIAL PRESSURE IN AUTOMATIC BLOOD PRESSURE MEASUREMENTS

FIELD OF THE INVENTION

This invention relates to the automatic measurement of blood pressure, and more particularly to identifying the mean arterial blood pressure despite the presence of artifact in the blood pressure measurements.

BACKGROUND ART

Automatic blood pressure monitors are commonly used to periodically measure the blood pressure of a patient. In most automatic blood pressure monitors, a pressure cuff is attached to a patient's arm over the brachial artery. The cuff is first pressurized with an applied pressure that is high enough to substantially occlude the artery. The cuff pressure is then gradually reduced, either continuously or in increments. As the pressure is reduced to systolic pressure, the flow of blood through the brachial artery beneath the cuff increases substantially.

When the blood flows through the brachial artery following each contraction of the heart, it imparts a pulsatile movement to the wall of the artery. This pulsatile movement is coupled to a blood pressure cuff extending over the artery as minute changes in cuff pressure, which are known as oscillometric pulses. Automatic blood pressure monitors can use these oscillometric pulses to indicate a patient's blood pressure. Conventional automatic blood pressure monitors measure and record the amplitude of the oscillometric pulses at a large number of discrete cuff pressures. After the blood pressure measurement has been completed, a recorded table contains the oscillometric pulse amplitude at each cuff pressure.

In theory, the systolic, diastolic and mean blood pressure can then be determined from the values in the table using empirical definitions of these parameters as a function of the amplitudes of these oscillometric pulses. However, blood pressure measurements are often adversely affected by artifact, generally produced by patient movement. Motion-induced artifact can substantially alter the measured amplitude of oscillometric pulses thus introducing inaccuracies in the measurement of oscillometric pulse amplitudes.

Techniques have been developed to determine the systolic and diastolic pressures even in the presence of artifact. However, it is substantially more difficult to determine the mean arterial pressure in the presence of artifact. The mean blood pressure occurs at the point where the oscillometric pulse has the largest amplitude. As mentioned above, artifact induced noise often obscures the largest oscillometric peaks by either making the peak oscillometric pulse appear to be smaller or by making other oscillometric pulses appear to be larger. It is thus often not possible to determine the peak oscillometric pulse by direct measurement. As a result, while the systolic and diastolic pressures can usually be accurately obtained using automatic blood pressure monitors, it is often not possible to obtain accurate measurements of mean arterial pressure using conventional automatic blood pressure monitors.

DISCLOSURE OF THE INVENTION

The primary object of the invention to provide a method and apparatus for allowing an automatic blood pressure monitor to accurately determine the mean arterial pressure despite the presence of artifact.

It is another object of the invention to provide a method and apparatus for allowing an automatic blood pressure monitor to accurately determine mean arterial pressure using the same data that is already collected in conventional automatic blood pressure monitors.

These and other objects of the invention are provided by a system for determining the mean arterial pressure using data collected by an automatic blood pressure monitor. The system includes an air pump, a valve and a pressure transducer pneumatically coupled to a blood pressure cuff. The pressure transducer generates a signal indicative of the air pressure in the blood pressure cuff and a signal corresponding to a oscillometric pulses detected in the cuff. A processor energizes the air pump to inflate the blood pressure cuff, periodically energizes the valve to incrementally reduce the air pressure in the blood pressure cuff, and records each pressure of the blood pressure cuff at which a measurement was taken as well as the amplitude of the oscillometric pulses at that cuff pressure. At the end of the blood pressure measurement, the processor has recorded a table of cuff pressures and corresponding oscillometric pulse amplitudes. The processor then uses an algorithm to calculate not only the systolic and diastolic pressures in a conventional manner, but also to calculate the mean arterial pressure using oscillometric pulse data in addition to the recorded peak oscillometric pulse. Basically, the processor interpolates the data in the table to determine the cuff pressures on each side of the measured peak oscillometric pulse amplitude at which the oscillometric pulse amplitudes are a predetermined percentage of the measured peak oscillometric pulse amplitude. The processor then calculates the mean arterial pressure as the average of the two interpolated cuff pressures.

BEST MODE FOR CARRYING OUT THE INVENTION

Figure 1:
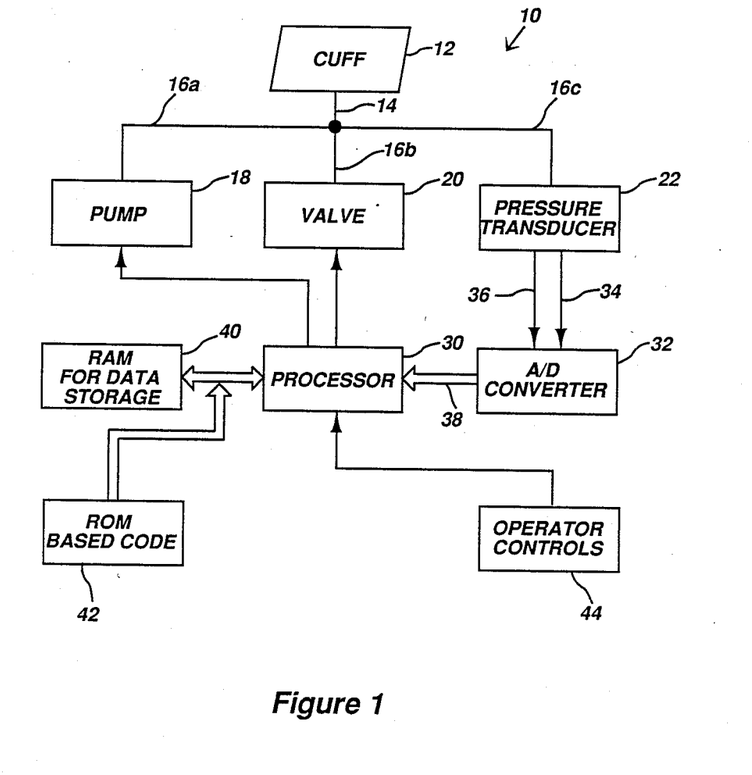
FIG. 1 is a block diagram of a system of automatically making blood pressure measurements with oscillometric techniques using conventional hardware.

One embodiment of a system for calculating the mean arterial pressure in an automatic blood pressure measuring system is illustrated in FIG. 1. The system 10 is composed of a number of hardware components, all of which are conventional. The system includes a conventional blood pressure cuff 12 in fluid communication with conduits 14 and 16, a conventional pump 18, a conventional valve 20, and a conventional pressure transducer 22. The pump 18 and valve 20 are operated by a conventional microprocessor 30.

As explained in greater detail below, during operation of the automatic blood pressure measuring system, the blood pressure cuff 12 is inflated to a pressure that is greater than systolic as indicated by the pressure transducer 22. The valve 20 is then opened, usually for a predetermined period, although it may be continuously open to allow a slight leakage of air from the blood pressure cuff 12. However, the valve 20 normally allows air to escape from the cuff 12 fairly rapidly in relatively small increments. As the pressure in the cuff 12 is reduced, either gradually or incrementally, the pressure in the cuff 12 is measured by the pressure transducer 22.

The pressure in the blood pressure cuff 12 consists of two components, namely, a relatively constant, or "D.C., component and a relatively variable, or "A.C.", component. The relatively constant component is a function of the pressure in the blood pressure cuff 12. The relatively variable component is produced by the minute change in the pressure of the cuff 12 as the blood pressure wave moves through the blood vessels beneath the cuff 12 following each contraction of the heart. Thus, the relatively constant D.C. component of the pressure in the cuff 12 can be used as an indication of cuff pressure, while the relatively variable A.C. component of the pressure in cuff 12 can be used as an indication of an oscillometric pulse. The pressure transducer 22 therefore generates two output signals; a DC output signal applied to an A/D converter 32 through line 34 and an AC output signal applied to the analog-to-digital converter 32 through line 36. The signal applied through line 34 is thus an indication of cuff pressure while the signal applied through line 36 is produced by the oscillometric pulse. The analog-to-digital converter 32 digitizes the DC and AC signals and outputs digital words indicative of their values through a bus 38 to the microprocessor 30.

As mentioned above, the microprocessor 30 is of conventional variety and, as is typical with such devices, is connected to a random access memory 40, used for temporary storage of data, and to a read-only memory 42 that contains the software for operating the microprocessor 30. Operator controls 44 such as a keyboard or buttons, are also connected to the microprocessor 30.

Although the measuring system 10 illustrated in FIG. 1 utilizes a pressure transducer 22 outputting separate DC and AC pressure signals, it will be understood that other implementations are possible. For example, the pressure transducer 22 may output a single signal corresponding to both the steady-state and variable pressures in the cuff 12. After this signal is digitized by the analog-to-digital converter 32 and applied to the microprocessor 30, software-based algorithms in the microprocessor 30 can detect the steady-state component of the cuff pressure and the variable component variations in the cuff pressure.

Figure 2A:
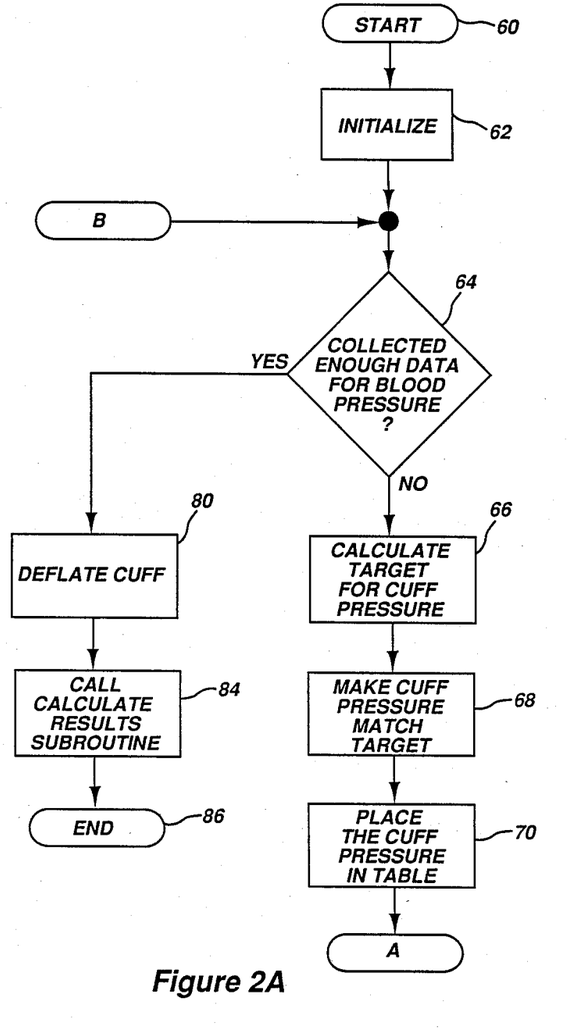
FIGS. 2A and 2B are flow charts of software used to program a microprocessor to operate the hardware illustrated in FIG. 1 in order to determine the mean arterial pressure.
Figure 2B:
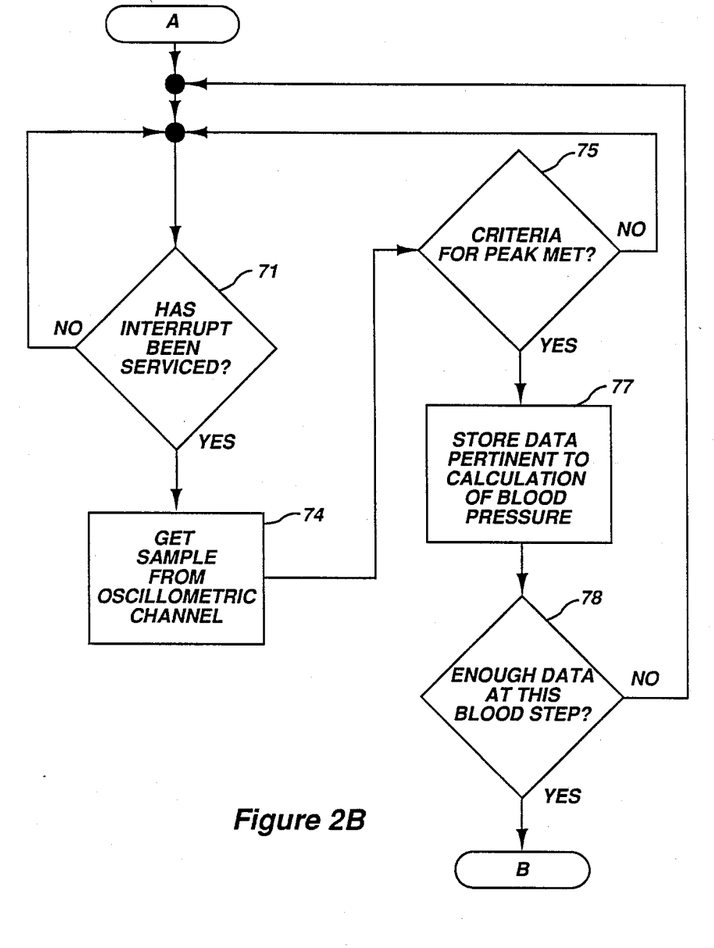

As explained above, the microprocessor 30 is controlled by software that is stored as a series of program instructions in the read-only memory 42. A flow chart from which object code can be easily and quickly written by one skilled in the art is illustrated in FIGS. 2A and 2B. With reference to FIG. 2A, the program starts at 60 either through an operator command, automatically at power-up or when called by another program stored in the read-only memory 42. As is conventional with microprocessor-based systems, the system is initialized at 62 to set up the software for subsequent processing, such as, for example, establishing tables that will subsequently contain data, by setting flags and by setting variables to known values. The program then checks at 64 to determine if enough data has been collected to provide a blood pressure measurement. The decision block 64 is first encountered prior to obtaining any blood pressure data. Thus, when the program initially encounters decision block 64, enough data for a blood pressure determination will not have been collected so that the program will branch to 66 to calculate a target value for the pressure in the blood pressure cuff 12 (FIG. 1). The target pressure for the cuff 12 will, of course, be in excess of the systolic pressure. The microprocessor 30 then energizes the pump 18 (FIG. 1) at 68 while measuring the DC signal output from the pressure transducer 22 as digitized by the analog-to-digital converter 32. The microprocessor continues to energize the pump 18 at 68 until the cuff pressure is equal to the target pressure. On subsequent passes through steps 66 and 68, the target pressure calculated at 66 will be lower than the initial pressure so that the microprocessor 30 will energize the valve 20 at 68 to reduce the pressure in the cuff 12 to the target pressure. Regardless of whether the pressure in the cuff 12 is increased to the starting value or whether it is being incrementally decreased after reaching the starting value, the cuff pressure is recorded in a table at 70 so that it can later be correlated with the measured amplitudes of the oscillometric pulses, as explained below.

The microprocessor 30 is interrupt driven in a conventional manner so that it periodically performs a clock driven interrupt service routine. The main program progresses from 70 in FIG. 2A to 71 in FIG. 2B until the interrupt has been serviced. During the interrupt, the program then samples the digitized AC signal output by the transducer at 74 and establishes the proper criteria for a set of samples being considered an oscillometric pulse. The program then checks at 75 to see if the criteria established at 74 are met. The criteria for determining if a set of samples is characteristic of an oscillometric pulse are conventional and are thus not explained herein. If the samples are not characteristic of an oscillometric pulse, the program returns to 71 to await another interrupt. If the samples do have the characteristics of an oscillometric pulse, the program branches to 77 to store the amplitude of the oscillometric pulse in the table in which the cuff pressure was recorded at 70 so that the amplitude of the oscillometric pulse is correlated with the cuff pressure at which the oscillometric pulse occurred. The program then checks at 78 to see if enough data had been collected at a the current cuff pressure, i.e., does the oscillometric peak meet the amplitude or timing constraints of the algorithm? If enough data have not been collected, the program returns to 71 to await another interrupt, and then collects another sample at 74 as explained above before once again checking for sufficient data at 78. If the program determines at 78 that all of the pertinent data for each oscillometric pulse have been collected, the program returns to 64 to check if data for enough oscillometric pulses have been collected to determine the patient's blood pressure.

The program will continue to loop through 64–78 until sufficient data have been obtained that the patient's blood pressure can be calculated. The data stored in the table after sufficient data have been obtained at several cuff pressures may appear, for example, as:

| CUFF PRESSURE | PULSE AMPLITUDE |
|---|---|
| 150 | 0 |
| 140 | 5 |
| 130 | 9.2 |
| 120 | 10 |
| 110 | 9.7 |
| 100 | 7.5 |
| 90 | 5 |
| 80 | 2.5 |
| 70 | 0 |

After the program determines at 64 that the data from all of the oscillometric pulses have been obtained, the program will then branch from 64 to 80, where the microprocessor 30 will continuously actuate the valve 20 to deflate the cuff 12. The program then calls a "CALCULATE RESULTS" subroutine, At 84 to cause the program to jump to a subroutine to calculated the mean arterial pressure as explained below. After the mean arterial pressure has been calculated in the "CALCULATE RESULTS" subroutine, the subroutine returns to main program where it terminates at 86 until another blood pressure measurement is to be made.

Figure 3:
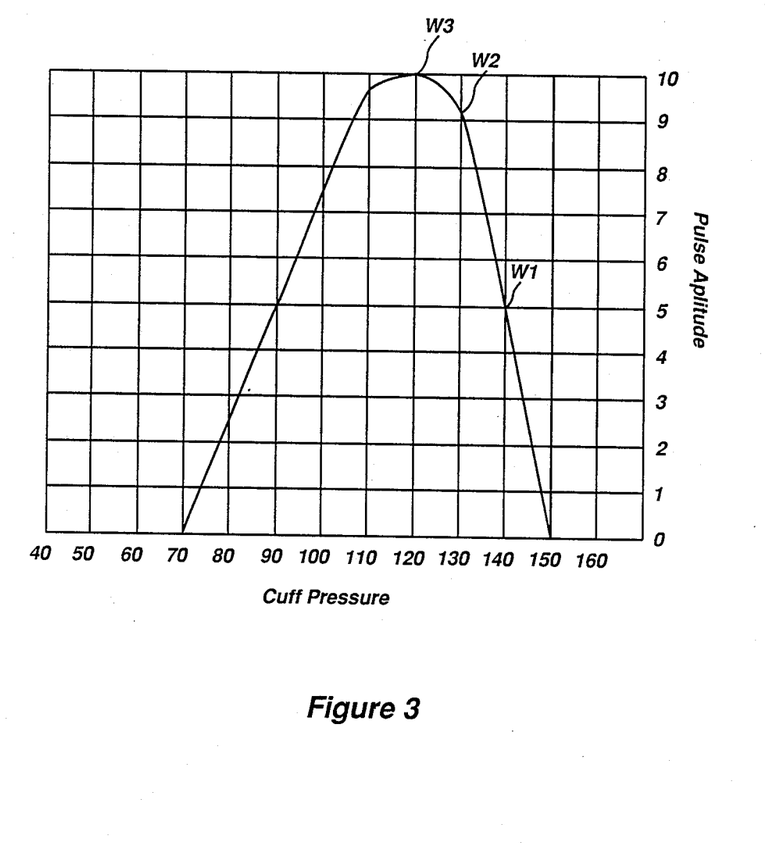
FIG. 3 is a graph showing a typical blood pressure profile and illustrating the manner in which the mean arterial pressure is determined in accordance with the invention.

The manner in which the inventive system determines the mean arterial pressure is illustrated in FIG. 3. FIG. 3 is a graph showing a typical blood pressure profile. The profile is shown with the cuff pressure on the X axis and the amplitude of the oscillometric pulses on the Y axis. In a typical blood pressure measurement, the cuff pressure is first pressurized to a relaitvely high value, and the cuff pressure is then incrementally reduced with the amplitude of the oscillometric pulses being measured at each cuff pressure. The mean arterial pressure is the pressure at which the amplitude of the oscillometric pulses peak, which, for the example illustrated in FIG. 3, is apparently an amplitude of 10 at a cuff pressure of 120. The rate of change in the oscillometric pulse amplitude at pressures above the peak is roughly twice the rate of change below the peak, as illustrated in FIG. 3. It has been empirically determined that the systolic pressure occurs when the amplitude of the oscillometric pulses is one-half the peak oscillometric pulse amplitude. Thus, for the example illustrated in FIG. 3, the amplitude of the oscillometric pulses is 5 (ie., one-half the peak oscillometric pulse amplitude of 10) at a systolic pressure of 140. It has also been empirically determined that the diastolic pressure occurs when the oscillometric pulses are three-quarters of the peak oscillometric pulse amplitude. Thus, for the example illustrated in FIG. 3, the oscillometric pulse amplitude is 7.5 (i.e., three-quarters of the peak amplitude of 10) at a diastolic pressure of 100.

As mentioned above, the mean arterial pressure occurs at the peak oscillometric pulse amplitude. Thus, in the profile illustrated in FIG. 3, one might conclude that the mean arterial pressure can be determined merely by detecting the peak oscillometric pulse amplitude of 10, which apparently occurs at 120. However, the mean arterial pressure cannot be determined this easily for two reasons. First, the peak oscillometric pulse amplitude may have occurred at a cuff pressure at which a blood pressure measurement was not made. Thus, for example, the true peak oscillometric pulse amplitude may be 10.5 occurring at 122. However, since a blood pressure measurement was not made at a cuff pressure of 122, the peak oscillometric pulse amplitude is not detected. Second, noise and artifact can often obscure the true oscillometric pulse amplitude, even when a blood pressure measurement is taken at the true means arterial pressure.

The inventive technique for determining the mean arterial pressure first determines the cuff pressure above and below the measured peak pressure at which the oscillometric pulse amplitude is 90% of the peak amplitude. In the example illustrated in FIG. 3, the oscillometric pulse amplitude is 9 (90% of the peak of 10) at cuff pressures of 130.5 and 106.8. The manner in which the cuff pressure at which the peak oscillometric pulse amplitude is 90% of the peak is determined is explained below. However, once the cuff pressures at which the oscillometric pulse amplitude is 90% of the peak oscillomertic pulse amplitude, the means arterial pressure is calculated by averaging these two pressures. Thus, in the example illustrated in FIG. 3, the means arterial pressure is 118.65 (i.e., one-half of 130.5+106.8).

As mentioned above, a blood pressure measurement may not have been taken at the cuff pressures at which the oscillometric pulse amplitude is equal of 90% of the peak oscillometric pulse amplitude. In the example illustrated in FIG. 3, the oscillometric pulse amplitude is equal to 90% of the peak at cuff pressures of 106.8 and 130.5. Yet blood pressure measurements were not made at these cuff pressures. Accordingly, the cuff pressures at which the oscillometric pulse amplitude is 90% of the peak are determined by interpolating between known cuff pressures and oscillometric pulse amplitudes. Thus, the cuff pressure on the systolic side of the profile at which the oscillometric pulse amplitude is equal to 90% of the peak is determined by interpolating between the known oscillometric pulse amplitudes at cuff pressures of 130 and 140. Similarly, the cuff pressure of the diastolic side of the profile at which the oscillometric pulse amplitude is 90% of the peak is determined by interpolating between the oscillometric pulse amplitudes at cuff pressures of 100 and 110.

Although the interpolation between the known values can be accomplished utilizing a number of techniques, a straight-line method provides adequate results. One technique for calculating the cuff pressure $P_s$ on the systolic side at which the oscillometric pulse amplitude is 90% of the peak using a straight-line interpolation of known cuff pressure and oscillometric pulse amplitude values is given by the formula:

$$CP_s = CP_{n-1} - (CP_{n-1} - CP_n)((OP_{n-1} - OP_s)/(OP_{n-1} - OP_n))$$

where $OP_s$ is 90% of the measured peak, or, using the values in the table above, 9. The term $CP_{n-1} - CP_n$ corresponds to the difference in cuff pressures at which the measurements were made (i.e., 140-130) while the term $(OP_{n-1} - OP_s)/(OP_{n-1} - OP_n)$ is a measure of how close to the cuff pressure $CP_n$ the oscillometric pulse amplitude is 90% of the peak. In the example illustrated in FIG. 3, the oscillometric pulse amplitude is 90% of the peak at a cuff pressure that is about 95% (i.e., (5-9)/(5-9.2)) of the difference between the cuff pressure of 140 and the cuff pressure of 130. Using the figures illustrated in FIG. 3, the cuff pressure at which the oscillometric pulse amplitude is 90% of the peak oscillometric pulse amplitude is about 130.5.

The cuff pressure on the diastolic side of the profile at which the oscillometric pulse amplitude is equal to 90% of the peak is interpolated using a similar formula. The formula for determining the cuff pressure $CP_d$ on the diastolic side of the profile is:

$$CP_d = CP_{m-1} - (CP_{m-1} - CP_m)((OP_{m-1} - OP_d)/OP_{m-1} - OP_m)).$$

where $OP_d$ is 90% of the measured peak, or, using the values in the table above, is 9. The terms in the above formula have the same significance as the similar terms explained above with respect to calculating the cuff pressure on the systolic side of the profile. Using the figures illustrated in FIG. 3, the cuff pressure on the diastolic side at which the oscillometric pulse amplitude is 90% of the peak oscillometric pulse amplitude is about 106.8. The mean oscillometric pressure is thus 118.65 (i.e. one-half the sum of 106.8 and 130.5).

As mentioned above, the mean arterial pressure is calculated in the "CALCULATE RESULTS" subroutine that is called at 84 in FIG. 2A. One embodiment of a "CALCULATE RESULTS" subroutine is illustrated in FIGS. 4A and 4B.

Figure 4A:
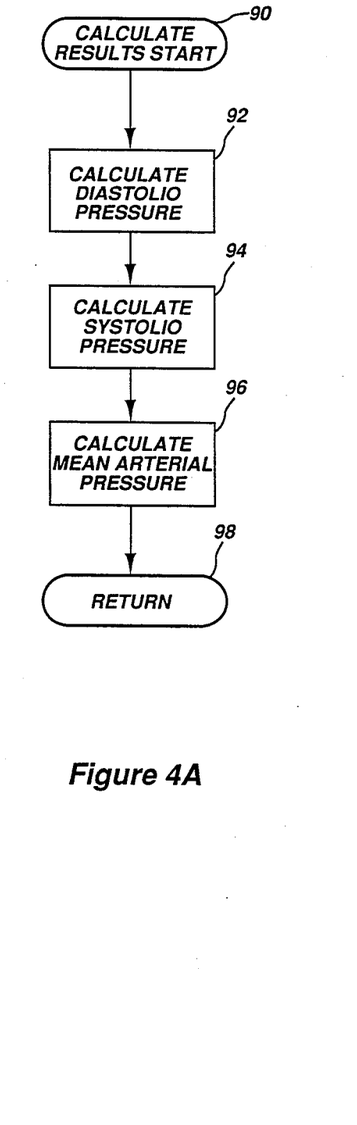
FIG. 4A, 4B and 4C are flow charts of a subroutine called by the program of FIG. 2 to calculate the systolic pressure, the diastolic pressure and the mean arterial pressure in the manner illustrated in FIG. 3.

With reference to FIG. 4A, the "CALCULATE RESULTS" subroutine is entered at 90 and a "CALCULATE DIASTOLIC PRESSURE" subroutine is called at 92. The subroutine for calculating the diastolic pressure is conventional and, since it is not required in the practice of the present invention, is not explained herein. The "CALCULATE RESULTS" subroutine then progresses to 94 to call a "CALCULATE SYSTOLIC PRESSURE" subroutine. Like the "CALCULATE DIASTOLIC PRESSURE" subroutine called at 92, the "CALCULATE SYSTOLIC PRESSURE" subroutine is conventional and not necessary for the practice of the present invention and is thus not explained herein. The program then branches to 96 where a "CALCULATE MEAN ARTERIAL PRESSURE" subroutine is called at 96. After the mean arterial pressure is calculated in the subroutine called at 96, the subroutine returns to the main program through 98.

Figure 4B:
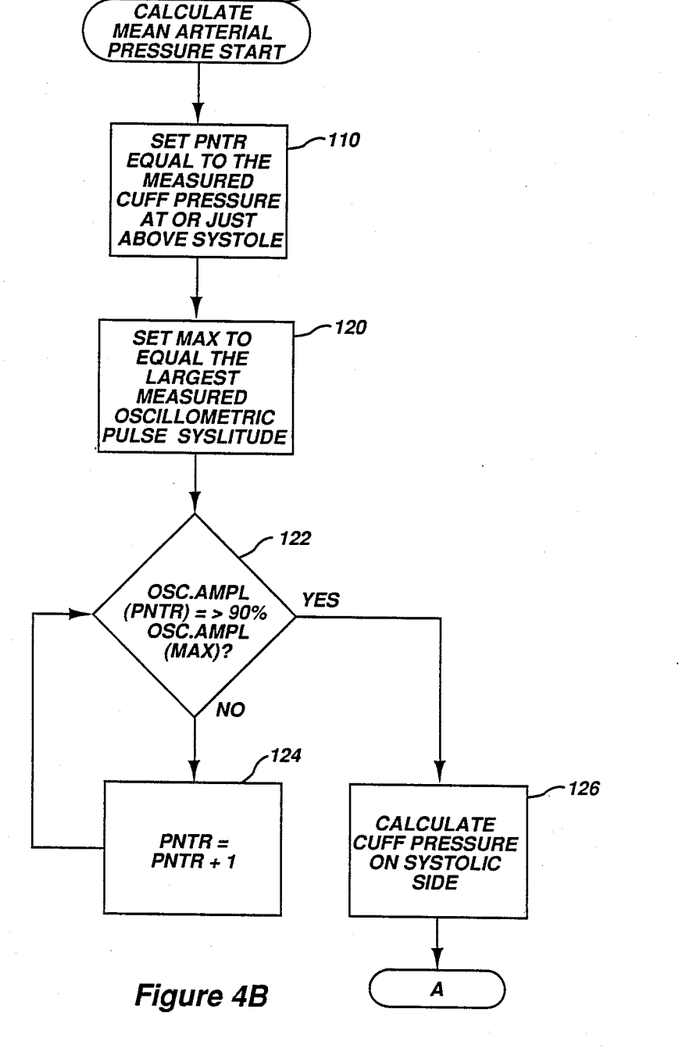

With reference to FIG. 4B, the "CALCULATE MEAN ARTERIAL PRESSURE" subroutine starts at 100, and a pointer is set at 110 to be equal to the measured cuff pressure that is just above systolic pressure. As a result, it is not necessary to consider cuff pressures that are above systolic pressure since the oscillometric pulse amplitude at systole must be less than one-half the peak oscillometric pulse amplitude and they thus cannot possibly be equal to 90% of the peak oscillometric pulse amplitude. In the example illustrated in FIG. 3, the pointer would be set to a cuff pressure of 140. The subroutine then sets the variable max to the largest-measured oscillometric pulse amplitude at 120. In the example illustrated in FIG. 3, the variable max is equal to 10. The subroutine then compares the oscillometric pulse amplitude at each cuff pressure to 90% of max at 122. If the oscillometric pulse amplitude at the cuff pressure of the current pointer is less then 90% of max, the subroutine branches to 124 where the pointer is incremented to the next-measured cuff pressure and returns to 122. The subroutine remains in the loop consisting of 122 and 124 until the oscillometric pulse amplitude at a cuff pressure is greater than 90% of max. The subroutine then branches to 126 to interpolate between the measured values to obtain the cuff pressure on the systolic side of the profile at which the oscillometric pulse amplitude is equal to 90% of the peak oscillometric pulse amplitude.

Figure 4C:
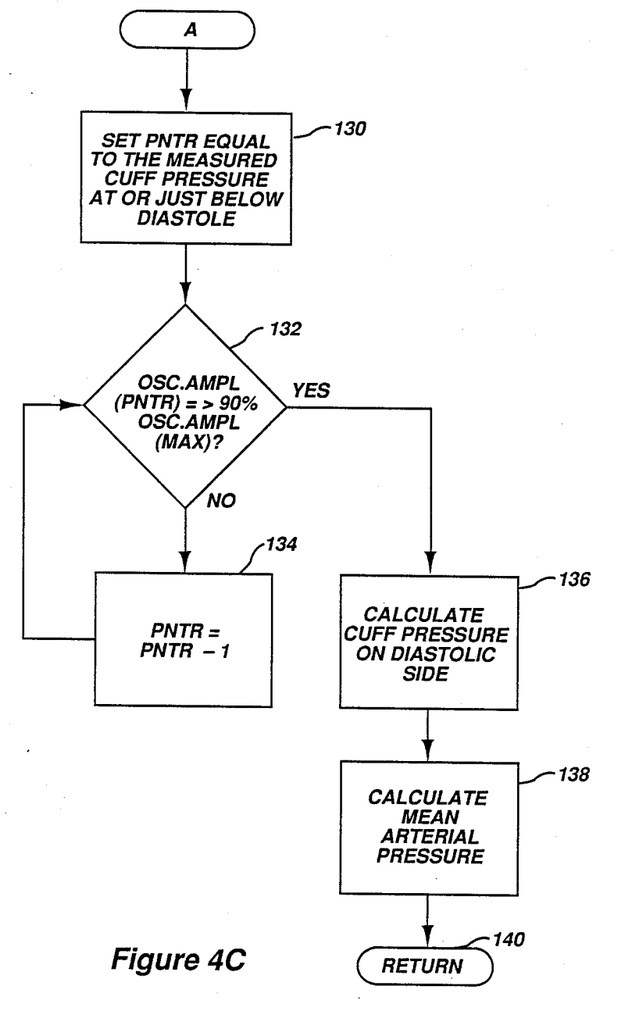

With reference to FIG. 4C the subroutine after 126 branches to 130 to determine the cuff pressure on the diastolic side of the profile at which the oscillometric pulse amplitude is equal to 90% of the peak oscillometric pulse amplitude. At 130, a pointer is set equal to the measured cuff pressure at or just below diastolic pressure. In the example illustrated in FIG. 3, the pointer would be set at 130 to 100. As explained above with reference to 110, setting the pointer at or just below the diastolic pressure avoids consideration of cuff pressures below deastole since the oscillometric pulse amplitude must be less than 75% of the peak oscillometric pulse amplitude. The subroutine then branches to 132 where the oscillometric pulse amplitude at the current cuff pressure is compared to 90% of max. If the oscillometric pulse amplitude at the cuff pressure currently being considered is not equal or greater than 90% of the peak amplitude, the program branches to 134 to decrement the pointer and then returns to 132 to compare the oscillometric pulse amplitude at the next cuff pressure to 90% of max. The subroutine thus remains in the loop 132, 134 until a cuff pressure having an oscillometric pulse amplitude greater than 90% of max occurs. The subroutine then branxhes to 136 to interpolate between the measured values to determine the cuff pressure at which the oscillometric pulse amplitude is equal to 90% of the peak. Finally, the subroutine calculates the mean arterial pressure at 138 using the formula given above before returning to the main program through 140.

It is thus seen that the inventive method and apparatus for determining the mean arterial pressure utilizes hardware found in conventional automatic blood pressure monitors and it calculates the mean arterial pressure using the same data that conventional blood pressure monitors already obtain to calculate the diastolic and systolic pressures. Furthermore, the system is able to accurately determine the mean arterial pressure despite the presence of noise and artifact in the monitoring process.

What is claimed:

1. A system for determining mean arterial pressure, comprising:

a blood pressure cuff;

an air pump pneumatically coupled to said blood pressure cuff;

a valve pneumatically coupled to said blood pressure cuff;

a pressure transducer pneumatically coupled to said blood pressure cuff, said pressure transducer generating a signal indicative of the air pressure in said blood pressure cuff and a signal corresponding to oscillometric pulses in said blood pressure cuff;

processor means connected to said pressure transducer and receiving said signal indicative of the air pressure in said blood pressure cuff and said signal corresponding to oscillometric pulses in said blood pressure cuff, said processor means energizing said air pump to inflate said blood pressure cuff, periodically energizing said valve to incrementally reduce the air pressure in said blood pressure cuff, recording the cuff pressure at which each measurement is made and the amplitude of the oscillometric pulses at such cuff pressure and calculating the mean arterial pressure by determining the oscillometric pulses having the largest amplitude, determining a first cuff pressure that is greater than the cuff pressure at which said largest oscillometric pulse occurred and at which the oscillometric pulses have a magnitude that is a first predetermined percentage of the magnitude of said oscillometric pulses having the largest amplitude, determining a second cuff pressure that is less than the cuff pressure at which said largest oscillometric pulses occurred and at which the oscillometric pulses have a magnitude that is a second predetermined precentage of the magnitude of said oscillometric pulses having the largest amplitude; and calculating the mean arterial pressure as the average of said first and second cuff pressures.

2. The system of claim 1 wherein said first and second predetermined percentages are equal to each other.

3. The system of claim 2 wherein said first and second predetermined percentages are 90 percent.

4. The system of claim 1 wherein said first cuff pressure is determined by interpolating between oscillometric pulse amplitudes and cuff pressures measured at a first pair of cuff pressures above and below said first cuff pressure, and said second cuff pressure is determined by interpolating between oscillometric pulse amplitudes and cuff pressures measured at a second pair of cuff pressures above and below said second cuff pressure.

5. The system of claim 4 wherein said interpolation is performed on a straight line basis between measured oscillometric pulse amplitudes and cuff pressures.

6. A system for determining the mean arterial pressure from a table of data containing the pressures of a blood pressure cuff at which blood pressure measurements were made and the amplitude of oscillometric pulses at each such blood pressure measurement, said system comprising:
  means for indentifying the oscillometric pulses in said table having the greatest amplitude and the cuff pressure at which the amplitude of said oscillometric pulses was measured;
  means for determining from the data in said table a first cuff pressure that is greater than the cuff pressure at which said largest oscillometric pulses occurred and at a cuff pressure at which oscillometric pulses have a magnitude that is a first predetermined percentage of the magnitude of the oscillometric pulses identified as having the largest amplitude;
  means for determining from the data in said table a second cuff pressure that is less than the cuff pressure at which said largest oscillometric pulses occurred and at a cuff pressure at which the oscillometric pulses have a magnitude that is a second predetermined precentage of the magnitude of the oscillometric pulses identified as having the largest amplitude; and
  means for calculating the mean arterial pressure as the average of said first and second cuff pressures.

7. The system of claim 6 wherein said first and second predetermined percentages are equal to each other.

8. The system of claim 7 wherein said first and second predetermined percentages are 90 percent.

9. The system of claim 6 wherein said first cuff pressure is determined by interpolating between oscillometric pulse amplitudes and cuff pressures measured at a first pair of cuff pressures above and below said first cuff pressure, and said second cuff pressure is determined by interpolating between oscillometric pulse amplitudes and cuff pressures measureed at a second pair of cuff pressures above and below said second cuff pressure.

10. The system of claim 9 wherein said interpolation is performed on a straight line basis between measured oscillometric pulse amplitudes and cuff pressures.

11. A method of determining the mean arterial pressure from a table of data containing the pressures of a blood pressure cuff at which blood pressure measurements were made and the amplitude of oscillometric pulses at each such blood pressure measurement, said method comprising:
  identifying the oscillometric pulses in said table having the greatest amplitude and the cuff pressure at which the amplitude of said oscillometric pulses was measured;
  determining from the data in said table a first cuff pressure that is greater than the cuff pressure at which said largest oscillometric pulses occurred and at a cuff pressure at which oscillometric pulses have a magnitude that is a first predetermined percentage of the magnitude of the oscillometric pulses identified as having the largest amplitude;
  determining from the data in said table a second cuff pressure that is less than the cuff pressure at which said largest oscillometric pulses occurred and at a cuff pressure at which the oscillometric pulses have a magnitude that is a second predetermined percentage of the magnitude of the oscillometric pulses identified as having the largest amplitude; and
  calculating the means arterial pressure as the average of said first and second cuff pressures .

12. The method of claim 11 wherein said first and second predetermined percentages are equal to each other.

13. The method of claim 12 wherein said first and second predetermined percentages are 90 percent.

14. The method of claim 11 wherein said first cuff pressure is determined by interpolating between oscillometric pulse amplitudes and cuff pressures measured at a first pair of cuff pressure above and below said first cuff pressure, and said second cuff pressure is determined by interpolating between oscillometric pulse amplitudes and cuff pressures measured at a second pair of cuff pressures above and below said second cuff pressure.

15. The method of claim 14 wherein said interpolation is performed on a straight line basis between measured oscillometric pulse amplitudes and cuff pressures.

* * * * *

UNITED STATES PATENT AND TRADEMARK OFFICE
CERTIFICATE OF CORRECTION

PATENT NO. : 4,905,704

DATED : March 6, 1990

INVENTOR(S) : Richard A. Walloch

It is certified that error appears in the above-identified patent and that said Letters Patent is hereby corrected as shown below:

On the cover page, following "Inventor:", delete "Richard A. Walloch, Beaverton, Wash." and substitute therefor --Richard A. Walloch, Beaverton, Oregon--.

In claim 6, column 9, line 35, delete "Indentifying" and substitute therefor --identifying--.

In claim 6, column 9, line 53, delete "precentage" and substitute therefor --percentage--.

In claim 14, column 10, line 50, delete "pressure" and substitute therefor --pressures--.

Signed and Sealed this

Twenty-first Day of May, 1991

Attest:

HARRY F. MANBECK, JR.

Attesting Officer

Commissioner of Patents and Trademarks